United States Patent [19]

McKay

[11] 4,021,543
[45] May 3, 1977

[54] PROCESS FOR DISGUISING SALINE TASTE OF PHARMACEUTICALS AND PRODUCT THEREOF

[75] Inventor: Gene Darrell McKay, Wauconda, Ill.

[73] Assignee: Abbott Laboratories, North Chicago, Ill.

[22] Filed: Mar. 28, 1975

[21] Appl. No.: 563,020

[52] U.S. Cl. .................................. 424/180; 536/4
[51] Int. Cl.$^2$ ........................................ A61K 31/70
[58] Field of Search ................ 424/180, 153; 536/4

[56] References Cited

UNITED STATES PATENTS 3,337,404  8/1967  Polli et al. .......................... 424/153
3,793,461  2/1974  Yuen ................................. 424/180

OTHER PUBLICATIONS

Martin, *Pharmaceutical Dispensing*, 6th ed. Mack Publ. Co., 1966, pp. 259–267.

*Primary Examiner*—Lewis Gotts
*Assistant Examiner*—Cary Owens
*Attorney, Agent, or Firm*—Robert L. Niblack; Neil E. Hamilton

[57] ABSTRACT

Glucose polymers having an average chain length of 3 – 8 units are added to an electrolyte solution which normally has a saline taste in an amount to substantially disguise the saline taste of the electrolyte solution. Preferably, the polymer is added in an amount in the range of 15% to 50% by weight and the electrolyte solution contains the usual chloride salts of calcium, magnesium and potassium with the solution having a pH in the range of 3 – 6.

11 Claims, No Drawings

PROCESS FOR DISGUISING SALINE TASTE OF PHARMACEUTICALS AND PRODUCT THEREOF

BACKGROUND OF THE INVENTION

This invention relates to pharmaceutical electrolyte solutions. More particularly it relates to a process and product wherein the characteristic saline taste of the electrolyte solution is disguised by adding to the electrolyte solution a glucose polymer having an average short-chain length and particularly one wherein the glucose polymer is composed of 3 – 8 units.

The use of dextrose for masking saline taste in pharmaceutical preparations is well known. However, the use of dextrose for this purpose often causes diarrhea and other gastrointestinal disturbances. The advantage of utilizing a glucose polymer in place of dextrose for added caloric content without additional osmotic pressure problems is indicated in U.S. Pat. No. 3,793,461. The reduced sweetness of dextrins when compared to glucose is indicated in "The Lancet," Apr. 5, 1969, page 690. However, prior to this invention no one has utilized glucose polymers of average short-chain length to mask saline taste and provide a product which will obviate gastrointestinal problems as well as a product having good flavor with stability.

It is an advantage of the present invention to provide an oral electrolyte solution wherein the saline taste is substantially reduced. Other advantages are an oral electrolyte solution which is pleasing to the taste yet does not adversely affect the gastrointestinal system, does not have an unpleasing sweet taste and will afford an increased caloric intake.

SUMMARY OF THE INVENTION

The foregoing advantages are accomplished and the shortcomings of the prior art overcome by the present process and product produced therefrom wherein an oral electrolyte solution is combined with a glucose polymer having an average short-chain length in the amount of about 3 – 8 units with the glucose polymer being added in an amount to substantially disguise the saline taste of the electrolyte solution. The glucose polymer is normally added in the amount of at least 15% by weight and the electrolyte solution is preferably composed of the chloride salts of calcium, magnesium and potassium. The pH of the solution is preferably in the range of 3 – 6. A preferred method of composing the electrolyte solution with the glucose polymer is in heating the aqueous solution prior to intermixing with the electrolyte solution.

The following Examples are set forth for the purpose of illustrating the present invention and should not be construed to limit the invention to the precise ingredients, proportions, temperatures or other conditions specified.

In the following Examples the source of the glucose polymer which has an average chain length of 3 – 8 units is Polycose which is a trademark for a carbohydrate product manufactured by Ross Laboratories Division of Abbott Laboratories.

EXAMPLE 1

An aqueous solution is prepared containing the following ingredients:

| Materials | Amount |
| --- | --- |
| Polycose glucose polymer | 13.125 kg. |
| Calcium chloride | 8.46 g. |
| Magnesium chloride | 18.62 g. |
| Potassium chloride | 84.91 g. |
| Sodium lactate 60% w/w solution | 300.00 g. |
| Potassium lactate 60% w/w solution | 47.90 g. |
| Lactic acid 80% Food Grade | 14.18 g. |
| Water for injection | q.s. 70.00 l. |

Approximately 70% of the final volume of the water is placed in a suitable tank and the calcium chloride, magnesium chloride and potassium chloride are added thereto and dissolved with thorough mixing. Subsequently the sodium lactate, potassium lactate and lactic acid are added also and dissolved with mixing. The resulting solution is heated and the Polycose is added with thorough mixing. The resulting solution is cooled and the remaining water is added to bring the total volume to 70 liters. The pH of the resulting solution is adjusted to 5.0 (4.8 – 5.2 range) with hydrochloric acid and the adjusted solution prefiltered through a filter. The filtered solution is again filtered through a membrane filter which is connected in series to the prefilter. The filtered material is then filled into washed clean bottles and autoclave sterilized. It will have a caloric content of 0.75 calories per milliliter.

The following Example is presented as an alternative formulation which will provide 1.25 calories per milliliter. The materials are mixed and prepared in the same manner as indicated in the previous Example:

EXAMPLE 2

| Materials | Amount |
| --- | --- |
| Polycose glucose polymer | 21.875 kg. |
| Calcium chloride | 0.386 g. |
| Magnesium chloride | 11.98 g. |
| Potassium chloride | 64.87 g. |
| Sodium lactate 60% w/w solution | 238.61 g. |
| Potassium lactate 60% w/w solution | 100.32 g. |
| Lactic acid 80% Food Grade | 23.65 g. |
| Water for injection | q.s. 70,00 l. |

In order to evaluate the flavor of the electrolyte-glucose polymer combination, a 32.5% w/v solution of the glucose polymer in combination with the electrolyte solution was prepared. The electrolyte solution was composed as follows:

EXAMPLE 3

| Materials | Amount |
| --- | --- |
| Polycose glucose polymer | 325.0 g. |
| Sodium chloride | .117 g. |
| Potassium chloride | 1.491 g. |
| Calcium chloride | .294 g. |
| Magnesium chloride | .407 g. |
| Sodium lactate 60% w/w | 5.233 g. |
| Water for injection | q.s. ad 1000.0 ml. |

A suitable control was provided utilizing 5% dextrose in combination with the same electrolyte and in turn certain taste characteristics of these two solutions were compared with the electrolyte solution only. The panel was composed of five people who were professionally trained in flavor evaluation. The results are shown in the following Table.

Table

| Characteristic | Electrolyte Plus 5% Dextrose | Electrolyte Plus Glucose Polymer | Electrolyte Only |
| --- | --- | --- | --- |
| Saline | Threshold to very slight | Threshold to very slight | Very slight |
| Sweet | Very slight | Very slight | — |
| Unidentified Flavor | — | Moderate | — |
| Body | Watery | Slight syrupy | Watery |
| Color | Colorless | Slight straw colored | Colorless |

The results indicated in the Table show that the samples containing the electrolyte plus the 5% dextrose and the electrolyte with the glucose polymer have essentially the same saline intensity. Both have a lower saline taste than the sample which contains the electrolyte only. The samples with the electrolyte in 5% dextrose and the electrolyte with the glucose polymer although having the same saline intensity, are distinctly different in overall taste. The panel reports that they have a slight sweet taste not present in the sample with the electrolyte only and in addition to being very slight saline tasting. The sample with the glucose polymer also had a different flavor not identified as well as having more body than either of the samples with the 5% dextrose or the electrolyte alone.

As a frame of reference, solutions of sodium chloride were used by the panel in determining the saline taste level of the test solutions. The flavor panel used a 0.4% sodium chloride solution for a "slight saline" standard; this was diluted to 0.2% and the dilution was found to be equivalent in saline taste to the saline taste of the sample which had the electrolyte only. The saline intensity of this dilution is considered very slight.

The panel reported that the electrolyte samples with the 5% dextrose and with the glucose polymer are less saline tasting than the 0.2% sodium chloride standard and were therefore assigned a saline intensity of "threshold to very slight." (The normal threshold value for saline is approximately 0.004 M or about 0.02% sodium chloride.)

These results indicate that the glucose polymer is equal to dextrose in disguising saline taste and in the concentration of 32.5% the polymer contributes an unidentified taste of its own to the electrolyte. Further, there is less flavor deterioration when employing the glucose polymer.

The term "short chain length" has been used in conjunction with the glucose polymer which is effective in masking the saline taste. While the preferred material utilized in this invention has an average chain length of 5 units, it should be understood that it is preferably composed of glucose units which vary from 3 to 8 units or greater. Further, while the glucose polymer is added in an amount of 32% by weight, this can vary and can be in the range of 15 to 50% by weight. It should also be understood that while certain salts have been utilized as composing the electrolyte solution, other physiologically acceptable salts such as the acetate, gluconate or phosphate could be substituted or could be used in combination with those indicated.

It will thus be seen that through the present invention there is now provided a method and product which can mask the saline flavor of electrolyte solutions without the adverse effects which would be caused in utilizing dextrose, namely, diarrhea and other gastrointestinal disturbances due to its osmotic properties. This is particularly evident where this material is administered to small children and infants. Further, the product is readily composed and the flavor is more stable when utilizing the glucose polymer than one containing a dextrose material. The present composition can contribute larger caloric uptake in an electrolyte product as compared to dextrose without the adverse effects caused by the osmotic pressure difference.

The foregoing invention can now be practiced by those skilled in the art. Such skilled persons will know that the invention is not necessarily restricted to the particular embodiments herein. The scope of the invention is to be defined by terms of the following claims as given meaning by the preceding description.

I claim:

1. A process for disguising saline taste in a pharmaceutical electrolyte solution comprising intermixing with a pharmaceutical electrolyte solution a glucose polymer having an average short-chain length of 3–8 units, in an effective amount to substantially disguise the saline taste of said pharmaceutical electrolyte solution without substantial adverse gastrointestinal effects.

2. The process as defined in claim 1 wherein said average chain length of said glucose polymer is 5 units.

3. The process as defined in claim 1 wherein said glucose polymer is added in an amount of at least 15% by weight based on the total weight of said solution.

4. The process as defined in claim 1 wherein said pharmaceutical electrolyte solution is composed of at least the chloride salts of calcium, magnesium and potassium.

5. The process as defined in claim 1 wherein said glucose polymer is dissolved in an aqueous solution and heated prior to intermixing with said pharmaceutical electrolyte solution.

6. The process as defined in claim 1 wherein the pH of said solution is adjusted to a range of 3 – 6.

7. A pharmaceutical electrolyte solution having a disguised saline taste comprising a pharmaceutical electrolyte solution and a glucose polymer having an average shortchain length of 3–8 units, said glucose polymer present in an effective amount to substantially disguise the saline taste of said electrolyte solution without substantial adverse gastrointestinal effects.

8. The composition as defined in claim 7 wherein the average chain length of said glucose polymer is 5 units.

9. The composition as defined in claim 7 wherein said glucose polymer is present in an amount of at least 15% by weight based on the total weight of said solution.

10. The composition as defined in claim 7 wherein said pharmaceutical electrolyte solution is composed of at least the chloride salts of calcium, magnesium and potassium.

11. The composition as defined in claim 7 wherein said solution has a pH in the range of 3 – 6.

* * * * *